United States Patent [19]

Banks et al.

[11] Patent Number: 5,374,252
[45] Date of Patent: Dec. 20, 1994

[54] LOCKING PNEUMONEEDLE

[75] Inventors: Thomas F. Banks, Santa Barbara, Calif.; William A. Mittelstadt, St. Paul, Minn.

[73] Assignee: Minnesota Mining and Manufacturing Company, St. Paul, Minn.

[21] Appl. No.: 190,235

[22] Filed: Feb. 1, 1994

Related U.S. Application Data

[63] Continuation of Ser. No. 808,152, Dec. 13, 1991, abandoned.

[51] Int. Cl.$^5$ ..................... A61M 5/178; A61B 10/00
[52] U.S. Cl. ..................... 604/158; 604/274; 128/754; 606/185
[58] Field of Search ............... 604/158, 162, 164, 165, 604/166, 169, 170, 246, 249, 256, 272, 274; 128/751, 752, 753, 754; 606/184, 185

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,001,638 | 5/1935 | Tornsjo . |
| 2,389,355 | 11/1945 | Goland et al. . |
| 2,496,111 | 1/1950 | Turkel . |
| 2,623,521 | 12/1952 | Shaw . |
| 2,630,803 | 3/1953 | Baran . |
| 3,454,006 | 7/1969 | Langdon . |
| 3,713,447 | 1/1973 | Adair . |
| 3,727,613 | 4/1973 | Sorenson et al. . |
| 3,774,604 | 11/1973 | Danielsson . |
| 4,068,659 | 1/1978 | Moorehead . |
| 4,163,446 | 8/1979 | Jamshidi . |
| 4,190,048 | 2/1980 | Sampson . |
| 4,254,762 | 3/1981 | Yoon . |
| 4,403,617 | 9/1983 | Tretinyak . |
| 4,431,426 | 2/1984 | Groshong et al. . |
| 4,535,773 | 8/1985 | Yoon . |
| 4,601,710 | 7/1986 | Moll . |
| 4,609,370 | 9/1986 | Morrison . |
| 4,617,929 | 10/1986 | Gill . |
| 4,617,933 | 10/1986 | Hasson . |
| 4,627,841 | 12/1986 | Dorr . |
| 4,630,616 | 12/1986 | Tretinyak ............ 604/165 X |
| 4,654,030 | 3/1987 | Moll et al. . |

(List continued on next page.)

FOREIGN PATENT DOCUMENTS

| | | |
|---|---|---|
| 0135364 | 3/1985 | European Pat. Off. . |
| 0265193 | 4/1988 | European Pat. Off. . |

(List continued on next page.)

Primary Examiner—Randall L. Green
Assistant Examiner—Mary Beth O. Jones
Attorney, Agent, or Firm—Gary L. Griswold; Walter N. Kirn; Jeffrey J. Hohenshell

[57] ABSTRACT

A safety pneumoneedle through which the abdomen can be inflated with fluid such as insufflating gas is described. The pneumoneedle comprises a housing having front and rear ends, exterior surfaces adapted to be manually grasped, inner surfaces defining an elongate cavity having a fluid passageway portion. The pneumoneedle includes a non-removable cannula having a proximal end sealingly and fixedly attached to the housing, and a sharpened distal end adapted to pierce tissue. A protector assembly is present which has a closed blunt distal end, a first abutment end surface, and a camming surface. The protector assembly is movable relative to the cannula between a protecting position with the blunt distal end of the protector extending beyond the sharp distal end of the cannula to restrict engagement between tissue and the sharp distal end of the cannula, and a retracted position with portions of the sharp distal end of the cannula extending beyond the blunt distal end of the protector to afford puncture of tissue. The pneumoneedle also includes a latching and release mechanism for positively locking the protector in the protecting position after the cannula has pierced tissue and for releasing the protector after it has been locked in the protecting position.

30 Claims, 5 Drawing Sheets

U.S. PATENT DOCUMENTS

| | | |
|---|---|---|
| 4,735,215 | 4/1988 | Goto et al. . |
| 4,747,831 | 5/1988 | Kulli . |
| 4,808,168 | 2/1989 | Warring . |
| 4,808,170 | 2/1989 | Thornton et al. . |
| 4,813,426 | 3/1989 | Haber et al. . |
| 4,828,547 | 5/1989 | Sahi et al. . |
| 4,846,785 | 7/1989 | Cassou et al. . |
| 4,850,973 | 7/1989 | Jordan et al. . |
| 4,869,717 | 9/1989 | Adair ............ 604/164 X |
| 4,902,280 | 2/1990 | Lander . |
| 4,906,236 | 3/1990 | Alberts et al. . |
| 4,907,599 | 3/1990 | Taylor . |
| 4,919,653 | 4/1990 | Martinez et al. . |
| 4,922,602 | 5/1990 | Mehl . |
| 4,931,042 | 6/1990 | Holmes et al. . |
| 4,952,207 | 8/1990 | Lemieux . |
| 4,973,312 | 11/1990 | Andrew . |
| 4,995,866 | 2/1991 | Amplatz et al. ............ 604/166 X |
| 5,036,860 | 8/1991 | Leigh et al. . |
| 5,098,388 | 3/1992 | Kulkashi et al. . |
| 5,104,381 | 4/1992 | Gresl et al. . |
| 5,104,382 | 4/1992 | Brinkerhoff et al. . |
| 5,116,353 | 5/1992 | Green . |
| 5,137,509 | 8/1992 | Freitas ............ 604/158 X |
| 5,139,485 | 8/1992 | Smith et al. ............ 604/158 |
| 5,152,754 | 10/1992 | Plyley et al. ............ 604/164 |
| 5,158,552 | 10/1992 | Borgia et al. ............ 604/165 |
| 5,226,426 | 7/1993 | Yoon ............ 128/753 |
| 5,226,891 | 7/1993 | Bushatz et al. ............ 604/165 |
| 5,292,310 | 3/1994 | Yoon ............ 604/158 |
| 5,295,993 | 3/1994 | Green ............ 604/164 X |

FOREIGN PATENT DOCUMENTS

| | | |
|---|---|---|
| 0350291 | 1/1990 | European Pat. Off. . |
| 0405883A1 | 1/1991 | European Pat. Off. . |
| 0495634A2 | 7/1992 | European Pat. Off. . |
| 696957 | 10/1940 | Germany . |
| 2544262 | 4/1977 | Germany . |
| 904635 | 8/1962 | United Kingdom . |
| 0878265 | 11/1981 | U.S.S.R. . |
| 1435246 | 11/1984 | U.S.S.R. . |
| WO89/03661 | 5/1989 | WIPO . |
| WO93/04632 | 3/1993 | WIPO . |
| WO93/04715 | 3/1993 | WIPO . |
| WO93/04716 | 3/1993 | WIPO . |
| WO93/04717 | 3/1993 | WIPO . |

LOCKING PNEUMONEEDLE

This is a continuation of application Ser. No. 07/808,152 filed Dec. 13, 1991, now abandoned.

TECHNICAL FIELD

The present invention relates generally to instruments for piercing tissue prior to laparoscopic surgery and more particularly to pneumoneedles for inflating the abdomen with fluid such as an insufflating gas prior to laparoscopic surgery.

BACKGROUND

Pneumoneedles are well known for use in medical procedures such as insufflation of the abdomen. Such a needle generally comprises a housing having manually engageable surfaces and proximal and distal ends; a stopcock valve located generally adjacent the proximal end of the housing; a needle having an elongate tubular body or lumen, and proximal and distal ends; and an elongate stylet situated generally within the needle lumen and having proximal and distal ends. The distal end of the stylet is blunt to restrict damage to tissue such as internal organs; and the distal end of the needle is sharp to pierce tissue.

The stylet is mounted to afford reciprocating longitudinal movement relative to the needle between a protecting position with the distal end of the stylet extending beyond the distal end of the needle and a retracted position with the distal end of the stylet retracted to expose portions of the sharp distal end of the needle to afford puncture of tissue (e.g. the abdominal wall) by the needle. A spring is present to bias the stylet toward the protecting position.

Prior art Veress-needles are disclosed in U.S. Pat. No. 4,808,168 to Warring. This and other Veress-needles of the prior art suffer many drawbacks. First, the stylets of the prior art pneumoneedles are merely biased toward a protecting position and cannot be positively retained in the protecting position. This is particularly important once the needle enters the abdominal cavity where it is near sensitive tissue and organs. If the prior art Veress-needles are pressed against sensitive tissue or an organ, there is a potential that the styler may deflect, thereby exposing the sharpened end of the needle with the attendant risk of undesirable tissue/organ damage from the sharp needle.

Another drawback of prior art Veress-needles is that the location of the stopcock valve is not desirable for some types of procedures. In one procedure, for example, after the pneumoneedle has apparently pierced the peritoneum, a saline/vacuum test would be conducted to determine whether the needle has actually entered the abdominal cavity. The saline/vacuum test comprises filling the barrel portion of the stopcock valve with saline solution (e.g. with a syringe) and then manually grasping the abdomen and lifting to expand the abdominal cavity. If the Veress-needle has entered the abdominal cavity, such action will create a vacuum and cause the saline solution to flow through the Veress-needle thereby indicating that the Veress-needle has entered the abdominal cavity.

Prior art Veress-needles such as those described in U.S. Pat. No. 4,808,168 encounter difficulties during such a test. For example, if such a Veress-needle is placed in a generally horizontal position, then the saline solution tends to spill, thereby rendering the saline/vacuum test useless and wasting valuable operating room time.

Another problem associated with prior art Veress-needles also arises out of the position of the stopcock relative to the housing. For example, the Veress-needles shown in U.S. Pat. No. 4,808,168 have a stopcock valve located generally adjacent a proximal end of the housing. The barrel portion of the stopcock is disposed generally coaxially with the longitudinal axis of the Veress-needle. Such a location is believed to provide an inconvenient position for connection to the tubing used for passage of the insufflating gas.

DISCLOSURE OF THE INVENTION

The present invention provides a safety pneumoneedle which a) provides a positively locking protector for restricting undesirable tissue or organ damage, and b) provides a stopcock valve disposed in a position which is convenient to use during a saline/vacuum test and which affords a convenient position and orientation for connecting the pneumoneedle to a tube for passage of insufflating gas.

According to the present invention there is provided a safety pneumoneedle through which the abdomen may be inflated with fluid such as insufflating gas.

The pneumoneedle comprises an elongate housing having front and rear ends, exterior surfaces adapted to be manually grasped in a dart-like fashion, inner surfaces defining an elongate cavity including a fluid passageway portion, and an actuator portion. There is a sealing surface at the juncture of the fluid passageway and actuator portions.

The housing also has a fluid conduit communicating with the fluid passageway portion of the elongate cavity. The fluid conduit has an axis disposed generally at an angle relative to a longitudinal axis of the housing. The fluid conduit opens through the exterior surface of the housing between the front and rear ends of the housing generally near the fluid passageway portion. The fluid conduit may be connected to a stopcock valve in an orientation that is convenient for conducting a saline/vacuum test and which is convenient for attaching the stopcock to insufflating gas tubing.

The pneumoneedle includes an elongate cannula having an inner surface defining a through passageway, and a proximal end sealingly and fixedly attached to the rear end of the housing. The through passageway communicates with the fluid passageway portion. The cannula also includes a sharpened distal end adapted to pierce tissue.

A protector assembly is present comprising an elongate protector having inner surfaces defining a passageway, a closed blunt distal end, and an opposite proximal end. The protector is mounted for sliding movement within the passageway of the cannula and has axially spaced proximal and distal fluid apertures. The protector assembly includes a carrier fixedly attached to the proximal end of the protector and disposed within the actuator portion of the housing cavity. The carrier has a sealing flange with a sealing flange surface at the juncture between the protector and the carrier. The carrier also has latching members extending axially of the housing cavity toward the front end of the housing. The latching members have a first abutment end surface, and include a camming surface disposed adjacent and intersecting the first abutment end surface.

The protector assembly is axially slidable within the housing cavity relative to the cannula between a protecting position and a retracted position. In the protecting position: (a) the blunt distal end of the protector extends beyond the sharp distal end of the cannula to restrict engagement between tissue and the sharp distal end of the cannula, (b) the sealing flange is in sealing engagement with the sealing surface of the housing, (c) the distal fluid aperture of the protector is disposed beyond and spaced from the distal end of the cannula and (d) the proximal fluid aperture of the protector is disposed within the fluid passageway portion of the housing cavity. In the retracted position, portions of the sharp distal end of the cannula extend beyond the blunt distal end of the protector to afford puncture of tissue.

The pneumoneedle includes a latching and release mechanism for positively locking the protector in the protecting position and for releasing the protector after it has been locked in the protecting position. The latch and release mechanism restricts undesirable tissue damage as described below.

The latching and release mechanism comprises a locking pawl spring disposed within the actuator portion of the housing and fixedly attached at a proximal end to the housing. The locking pawl spring has a distal end. The locking pawl spring is mounted for movement between (1) a locking position with the distal end of the pawl spring engaged with the first abutment end surface of the latching members to prevent axial movement of the protector relative to the cannula and to lock the protector in the protecting position, and (2) a release position with the distal end of the locking pawl spring spaced from the first abutment end surface of the latching members to afford relative axial movement between the protector and the cannula to afford piercing of tissue by the sharp end of the cannula. The locking pawl spring is biased toward the locking position by, for example, its own inherent bias.

The pneumoneedle also includes a reset button member having an exposed end adapted to be manually pressed, a lock release camming surface, and a lock release shoulder surface generally intersecting the lock release camming surface. The lock release shoulder surface is adapted to retain the locking pawl spring in the release position until the camming surface of the protector assembly moves the locking pawl spring away from engagement with the lock release shoulder surface.

Portions of the reset button are axially slidable within the actuator portion of the housing cavity for movement between (1) a latched position with the exposed end of the reset button spaced from the front end of the housing and (2) a reset position with the exposed end of the reset button closer to the front end of the housing than in the latched position. A coil spring biases the protector toward the protecting position and biases the reset button toward the latched position.

In a preferred embodiment, the carrier comprises a carriage portion, the sealing flange and the latching members. The sealing flange of the carrier includes an elastomeric sealing member.

The latching members comprise a pair of spaced guide members defining a groove therebetween. The reset button comprises a body portion having an inner end opposite the exposed end, a pair of slots for receiving the guide members, and a reinforcing rib adapted to be received in the groove between the guide members.

Also in a preferred embodiment, the body portion of the reset button has a notch surface generally adjacent the inner end and an opposite shoulder surface axially spaced from the notch surface and disposed closer to the inner end than the lock release shoulder surface.

Figure 3:
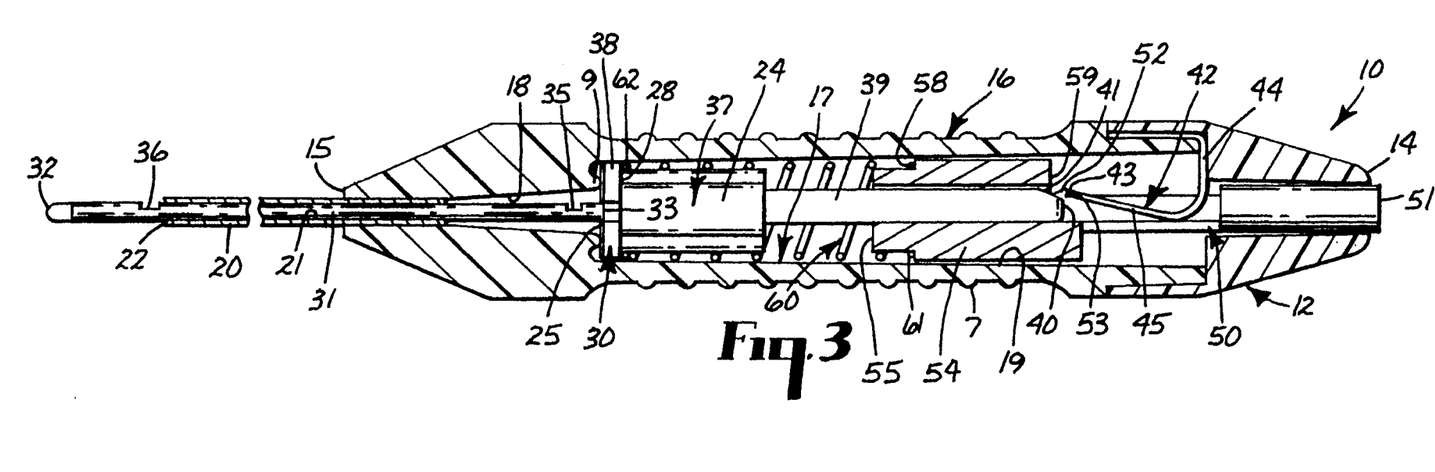

In operation, when the reset button is in the latched position and the protector assembly is in the protecting position (FIG. 6), the protector cannot move relative to the cannula; and thus the cannula is restricted from causing undesirable tissue damage. From this position, manual movement of the reset button toward the reset position will cause the lock release camming surface of the reset button to move the locking pawl spring from the locking position toward the release position and will then allow the locking pawl spring to engage the lock release shoulder surface (FIG. 3). In this position, the protector is now free to move relative to the cannula.

Figure 4:
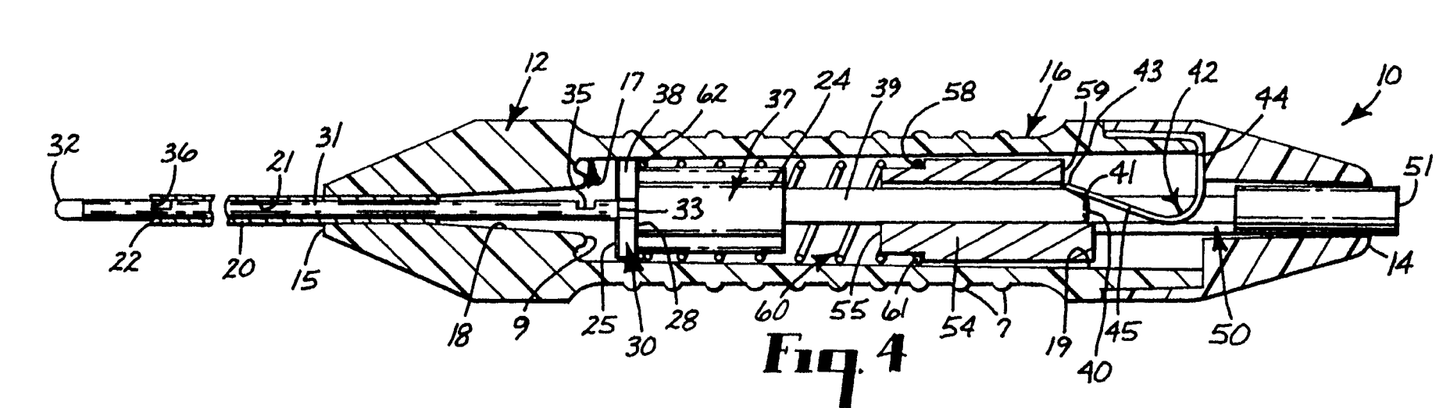
Figure 5:
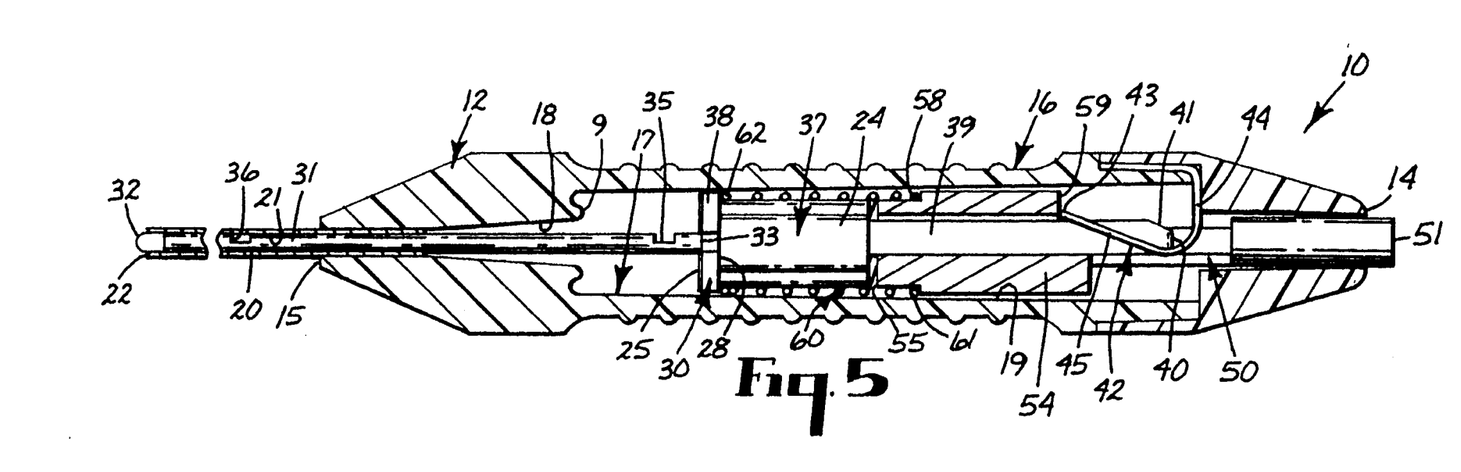

Next, when the protector is pressed against tissue (FIG. 4), the resistance of the tissue will cause the protector assembly to move axially toward the retracted position, ultimately exposing the sharp end of the cannula to afford piercing tissue (FIG. 5). Such action causes the camming surfaces on the carrier to move the locking pawl spring away from engagement with the lock release shoulder surface (FIG. 4). Moving the locking pawl spring away from engagement with the lock release shoulder surface affords movement of the locking pawl spring toward the locking position when the coil spring causes the protector assembly to move to the protecting position after resistance from the tissue is released (e.g. upon movement of the cannula into the abdominal cavity).

BRIEF DESCRIPTION OF THE DRAWINGS

The present invention will be further described with reference to the accompanying drawing wherein like reference numerals refer to like parts in the several views, and wherein:

FIGS. 3 through 6 are side views of the pneumoneedle of FIG. 1, taken approximately ninety (90) degrees from the top side view of FIG. 2, with portions broken away to show details and which sequentially illustrate the operation of pneumoneedle of FIG. 1 wherein:

FIG. 3 illustrates the pneumoneedle with the reset button member in a reset or armed position and with the pneumoneedle ready to be pressed against tissue;

FIG. 4 illustrates the pneumoneedle just after it is initially pressed against tissue, showing the protector assembly moved toward the front end of the housing and showing the reset button member in a triggered position;

FIG. 5 illustrates the pneumoneedle as it is pressed through the abdominal wall with the protector assembly in the retracted position;

FIG. 6 illustrates the pneumoneedle after it has been pressed into the abdominal cavity and after the resistance from tissue has ended, with the protector assembly in the protecting position, with the locking pawl spring in the locking position and with the reset button in the latched position.

DETAILED DESCRIPTION

Referring now to FIGS. 1 through 7 of the drawing, there is shown a preferred embodiment of safety pneumoneedle according to the present invention, generally designated by the reference character 10.

The safety pneumoneedle 10 is a device through which the abdominal cavity of a patient (e.g. human) can be inflated with fluid such as insufflating gas. The pneumoneedle 10 comprises an elongate housing 12 having a longitudinal axis A, front 14 and rear 15 ends, and exterior surfaces 16 generally cylindrical about the axis A.

Figure 7:
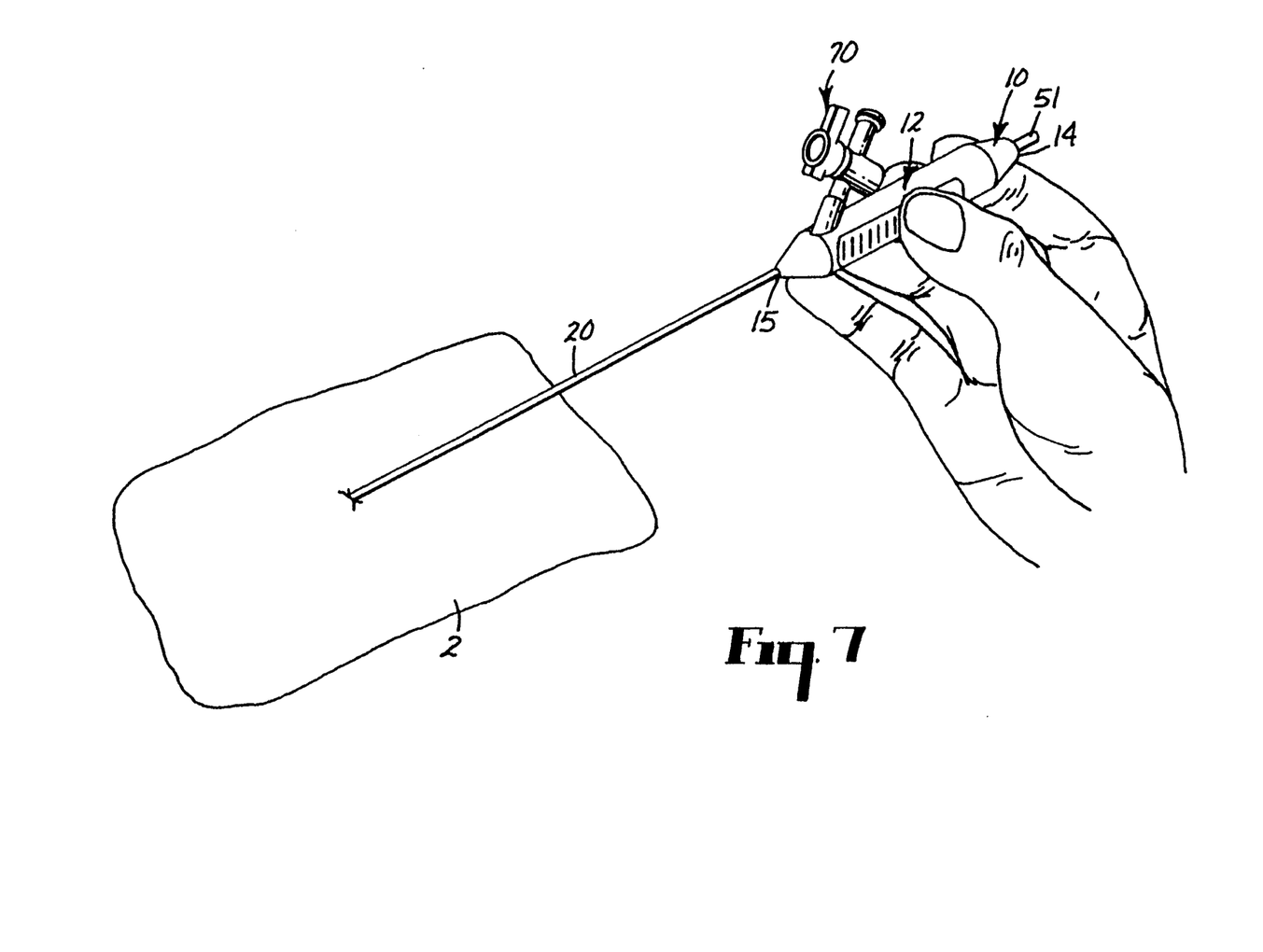
FIG. 7 is a perspective view illustrating a manually held pneumoneedle after it has punctured tissue with a barrel portion of the stopcock disposed for a saline/vacuum test.

The housing 12 may be manually grasped in a dart-like fashion (see FIG. 7). Alternatively the housing 12 may be grasped in a manner similar to that shown in FIG. 7 except that the two fingers that are the farthest from the thumb are curled between the housing 12 and the user's palm. The housing 12 may be constructed from any suitable material such as, but not limited to, polymers or metals or combinations thereof. For example, the housing 12 may be injected molded in several parts (e.g. a base portion and a cap portion) using an ABS plastic/polymer material such as the Cycolac GSM 2679F resin generally available from the General Electric Corporation of Pittsfield, Massachusetts. Optionally, the exterior surfaces 16 of the housing 12 may include a structured surface such as ribs 7 for enhancing manual grasping of the housing 12 in the manner shown, for example, in FIG. 7.

The housing 12 includes inner surfaces 17 defining an elongate cavity extending axially between the front 14 and rear 15 ends of the housing 12. The cavity includes a fluid passageway portion 18 adjacent the rear end 15, and an actuator portion 19 adjacent the front end 14. The actuator portion 19 preferably has a larger diameter than the fluid passageway portion 18 at the juncture of the portions 18 and 19. The inner surface 17 of the housing 12 defines a sealing surface 9 around the fluid passageway portion 18 at the juncture between the portions 18 and 19. The housing cavity opens through the exterior surfaces 16 of the housing 12 generally adjacent the front 14 and rear 15 ends of the housing 12.

The housing 12 also has a fluid conduit 8 (FIG. 2) communicating with the fluid passageway portion 18 of the elongate cavity. The fluid conduit 8 has an axis A' disposed generally at an angle relative to the longitudinal axis A of the housing 12. The fluid conduit 8 opens through the exterior surface 16 of the housing 12 between the front 14 and rear 15 ends of the housing 12 generally near the fluid passageway portion 18.

FIG. 7 illustrates a stopcock valve 70 in fluid communication with the fluid conduit 8. The location of the stopcock valve 70 is particularly desirable for some types of procedures. For example, to conduct the saline/vacuum test described above, a user may conveniently fill the barrel portion of the stopcock valve 70 with saline solution (e.g. with a syringe). When the pneumoneedle is placed in a generally horizontal position (as shown in FIG. 7), the barrel portion of the stopcock valve 70 is generally in a vertical orientation to restrict spillage of saline.

The location of the stopcock valve 70 is also believed to afford a convenient position and orientation for connecting the pneumoneedle to a tube for passage of insufflating gas. The location of the stopcock valve 70 is also believed to be beneficial in minimizing the potential for "kinks" in the tube for passage of insufflating gas.

The pneumoneedle 10 includes a tubular elongate cannula 20 having an inner surface 21 defining a through passageway, a proximal end sealingly and fixedly attached (e.g. by means of a Prism Instant Adhesive, such as product No.'s 401, 405, 406 or 454 generally available from LOCTITE corporation of Newington, Conn.) to the rear end 15 of the housing 12. The through passageway of the cannula 20 is in fluid communication with the fluid passageway portion 18 of the housing 12. The cannula 20 includes a sharpened distal end 22 adapted to puncture or pierce tissue, and a predetermined length between the proximal and distal 22 ends. The cannula 20 may comprise any suitable material such as but not limited to Stainless Steel. For example, the cannula 20 may comprise ASTM #304W Stainless Steel with an outer diameter of approximately 0.083 inches (2.1 millimeters), an inner diameter of approximately 0.067 inches (1.7 millimeters), and a length measured from the end 15 of the housing 12 to the distal end 22 of about 12 centimeters.

The pneumoneedle 10 includes a protector assembly 30 comprising a tubular elongate protector 31 having inner surfaces defining a fluid passageway, an outer surface, a closed blunt distal end 32, and an opposite proximal end 33. As shown in FIGS. 2 through 6, the blunt distal end 32 may be formed from a different piece than the rest of the protector 31. For example the distal end 32 may be formed from a plastic or polymeric member which is adhesively adhered to the remaining portion of the protector 31. Alternatively the blunt distal end 32 and the rest of the protector 31 may be formed from a single monolithic metal (e.g. Stainless Steel) piece by methods known in the art such as, but not limited to spin welding or mechanical deformation processes.

The protector 31 has a length between ends 32 and 33 that exceeds the predetermined length of the cannula 20 between the proximal and distal 22 ends of the cannula 20. The protector 31 is mounted for longitudinal sliding movement within the passageway of the cannula 20 and has axially spaced proximal 35 and distal 36 fluid apertures extending between the protector's 31 inner and outer surfaces. The apertures 35 and 36 open into the protector's 31 passageway adjacent the blunt distal 32 and opposite proximal 33 ends respectively.

The protector 31 may be constructed from any suitable material such as but not limited to a polymer or a metal. For example, the protector 31 may comprise an ASTM #304W Stainless Steel with an inner diameter of approximately 0.053 inches (1.35 millimeters) and an outer diameter of approximately 0.065 inches (1.65 millimeters) and a length of 5.78 inches (14.7 centimeters) measured between the proximal end 33 and the distal end 32. Alternatively, rather than a single aperture 35 or 36 at each of the ends 32 and 33 of the protector 31, the protector 31 may comprise a pair of apertures (not shown) at each of the ends 32 and 33 of the protector 31. In another alternative, the protector 31 may include a channel (not shown) which extends from a position generally adjacent one end 33 of the protector 31 to a position generally adjacent the other end 32 of the protector 31.

The protector assembly 30 includes a carrier 37 fixedly attached (e.g. by means of a Prism Instant Adhesive, such as product No.'s 401, 405, 406 or 454 generally available from LOCTITE corporation of Newington, Conn.) to the proximal end 33 of the protector 31 and disposed within the actuator portion 19 of the housing cavity.

The carrier 37 has a sealing flange 38 with a sealing flange surface at the juncture between the protector 31 and the carrier 37 adapted for abutting the sealing surface 9 of the housing 12. The carrier 37 has latching members 39 extending axially of the housing cavity toward the front end 14. The latching members 39 have a first abutment end surface 40 disposed generally at a right angle with respect to the axis A, and include a camming surface 41 disposed at an acute angle with respect to the axis A adjacent and intersecting the first abutment end surface 40. The carrier 37 may be constructed from any suitable material, such as but not limited to, a polymer material such as LEXAN HP1 generally available from the General Electric Corporation of Pittsfield, Mass. The carrier 37 may be bonded to the cannula 20 by means well known in the art, such as, for example, by means of a Prism Instant Adhesive, such as product No.'s 401, 405, 406 or 454 generally available from LOCTITE corporation of Newington, Conn.

The protector assembly 30 is axially slidable within the housing cavity relative to the cannula 20 between a protecting position (FIG. 6) with the blunt distal end 32 of the protector 31 extending beyond the sharp distal end 22 of the cannula 20 to restrict engagement between tissue and the sharp distal end 22 of the cannula 20 and a retracted position (FIG. 5). When the protector assembly 30 is in the protecting position: (1) the sealing flange 38 has surfaces in sealing engagement with the sealing surface 9 of the housing 12; (2) the distal fluid aperture 36 of the protector 31 is disposed beyond and spaced from the distal end 22 of the cannula 20; (3) the proximal fluid aperture 35 of the protector 31 is disposed within the fluid passageway portion 18 of the housing cavity; and (4) the blunt distal end 32 of the protector 31 extends beyond the sharp distal end 22 of the cannula 20 to restrict engagement between tissue 2 and the sharp distal end 22 of the cannula 20.

When the protector assembly 30 is in the retracted position (FIG. 5), portions of the sharp distal end 22 of the cannula 20 extend beyond the distal end 32 of the protector 31 to afford puncture of tissue.

The pneumoneedle 10 also includes a latching and release mechanism or means for positively locking the protector 31 in the protecting position and for releasing the protector 31 after it has been locked in the protecting position.

The latching and release means comprises a locking pawl spring 42 disposed within the actuator portion 19 of the housing and fixedly attached (e.g. by mechanically sandwiching the pawl spring 42 between the cap portion of the housing 12 and the rest or base portion of the housing 12, see FIGS. 3 through 6) at a proximal end to the housing 12. The locking pawl spring 42 also has a distal end 43.

The locking pawl spring 42 may be constructed from any suitable material such as, but not limited to #302 ASTM Stainless Steel. Alternatively, the locking pawl spring 42 and at least portions of the housing may be a unitary, monolithic structure constructed from, for example, an injection molded polymer or polycarbonate material such as LEXAN HP1 generally available from the General Electric Corporation of Pittsfield, Mass.

The locking pawl spring 42 is mounted for movement between a locking position (FIG. 6) and a release position (FIGS. 2, 3, 4 and 5). In the locking position, the distal end 43 of the pawl spring 42 engages the first abutment end surface 40 of the latching members 39 to prevent axial movement of the protector 31 relative to the cannula 20 and to lock the protector 31 in the protecting position. In the release position, the distal end 43 of the locking pawl spring 42 is spaced from the first abutment end surface 40 of the latching members 39 to afford relative axial movement between the protector 31 and the cannula 20 to afford piercing of tissue by the sharp end 22 of the cannula 20. The locking pawl spring 42 is biased toward the locking position by its own inherent bias.

The locking pawl spring 42 preferably comprises a monolithic wire member having a pair of base portions 44 extending generally at an angle relative to the longitudinal axis A of the housing cavity, a pair of neck portions 45 extending at an angle relative to the base portions 44 and an end portion extending between the neck portions 45 and having the distal end 43.

The locking and release means also include a reset button member 50 having an exposed end 51 adapted to be manually pressed, a lock release camming surface 52 disposed at an acute angle with respect to the housing axis A, and a lock release shoulder surface 53 disposed generally at a right angle with respect to the housing axis A and intersecting the lock release camming surface 52. The lock release shoulder surface 53 retains the locking pawl spring 42 in the release position until cam surfaces 41 move toward the end 14 of the housing 12 (see FIG. 4).

Portions of the reset button 50 are axially slidable within the actuator portion 19 of the cavity for movement between a latched position (FIG. 6) with the exposed end 51 of the reset button 50 spaced from the front end 14 of the housing 12 and a reset or armed position (FIGS. 2 and 3) with the exposed end 51 of the reset button 50 closer to the front end 14 of the housing 12 than in the latched position.

Figure 6:
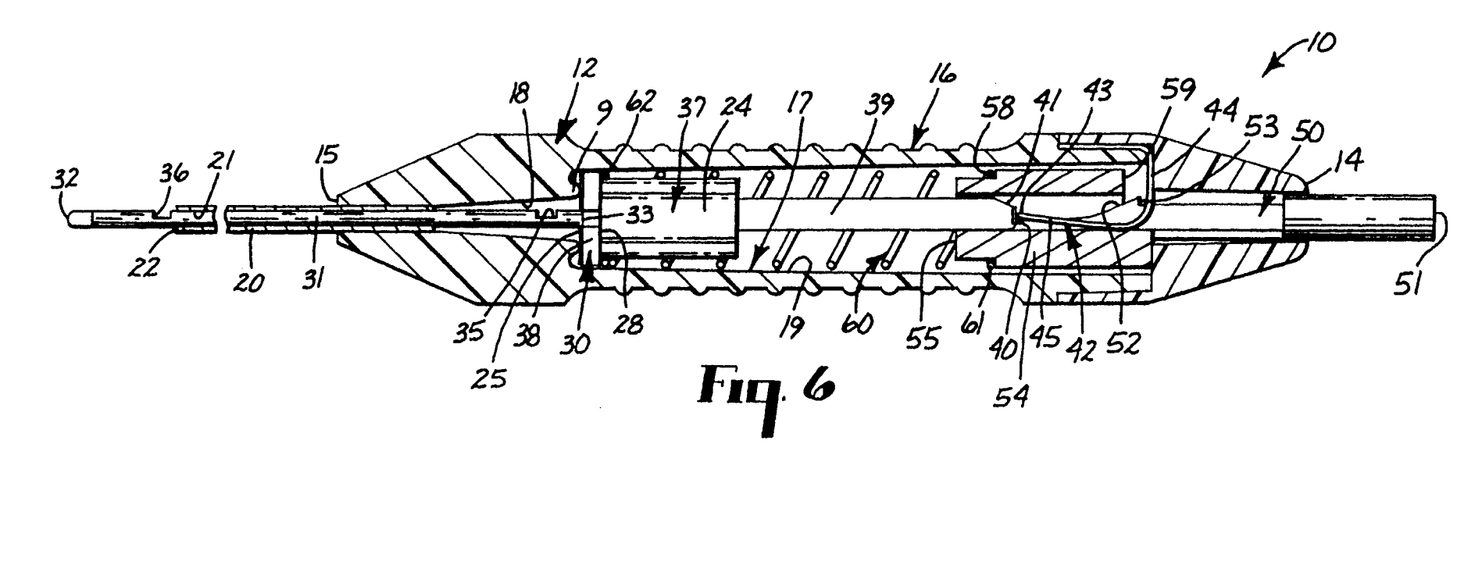

The pneumoneedle 10 also includes biasing means in the form of a coil spring 60 for biasing the protector assembly 30 toward the protecting position (FIG. 6) and for biasing the reset button member 50 toward the latched position (FIG. 6).

Preferably the carrier 37 comprises a carriage portion 24, the sealing flange 38 and the latching members 39. Also preferably, the sealing flange 38 has a surface 28 opposite the sealing surface, and the sealing flange 38 of the carrier 37 includes an elastomeric sealing member 25 constructed from any suitable sealing material such as, but not limited to an elastomer, Buna N rubber or silicone rubber. For example, the sealing member 25 may comprise a 2050 LSR silicone seal generally available from Mobay of Rosemont, Ill.

Figure 1:
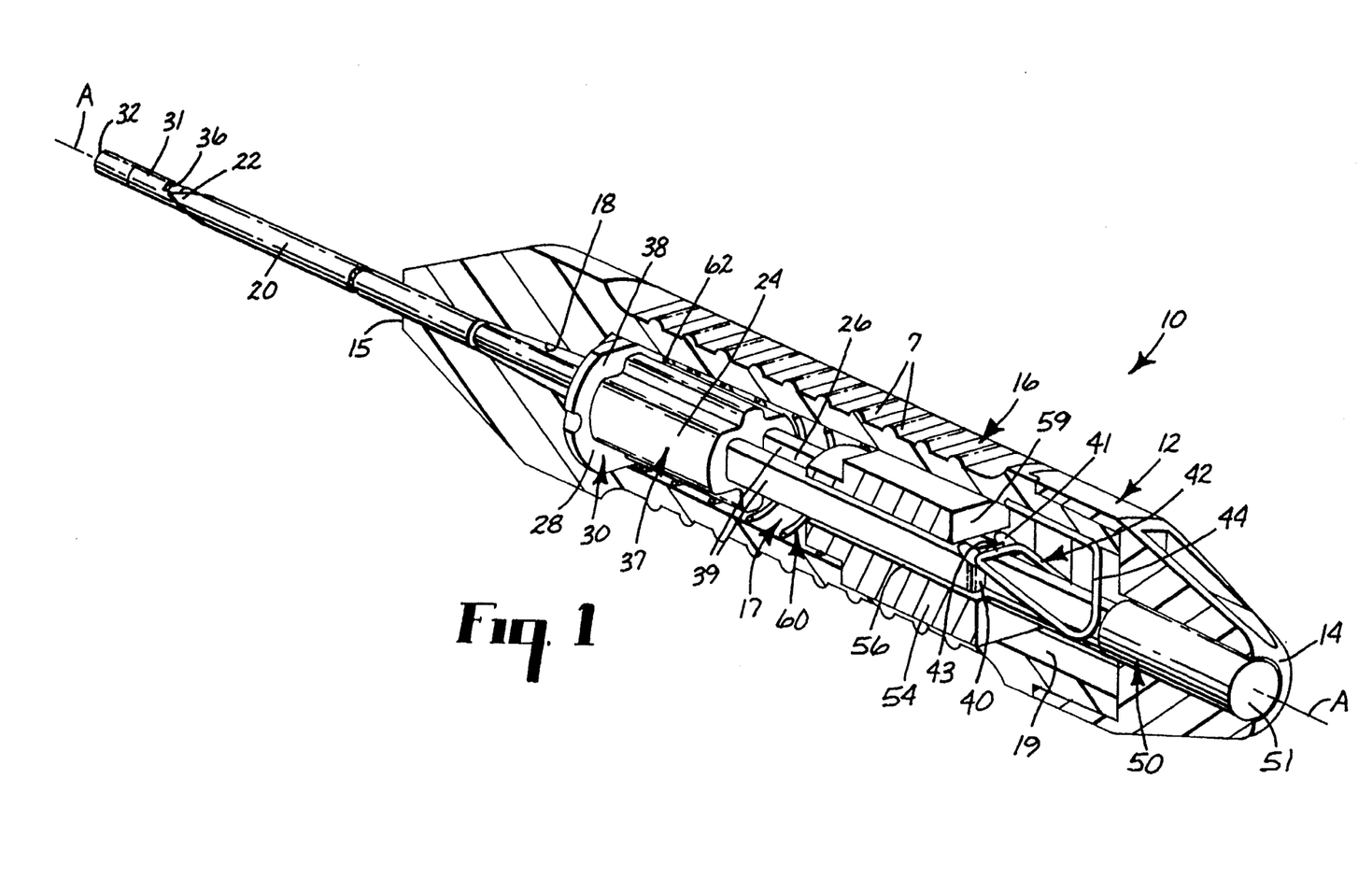
FIG. 1 is a perspective view of the pneumoneedle according to the present invention with portions broken away to show details of a protector assembly, reset button member, coil spring, and locking pawl spring.
Figure 2:
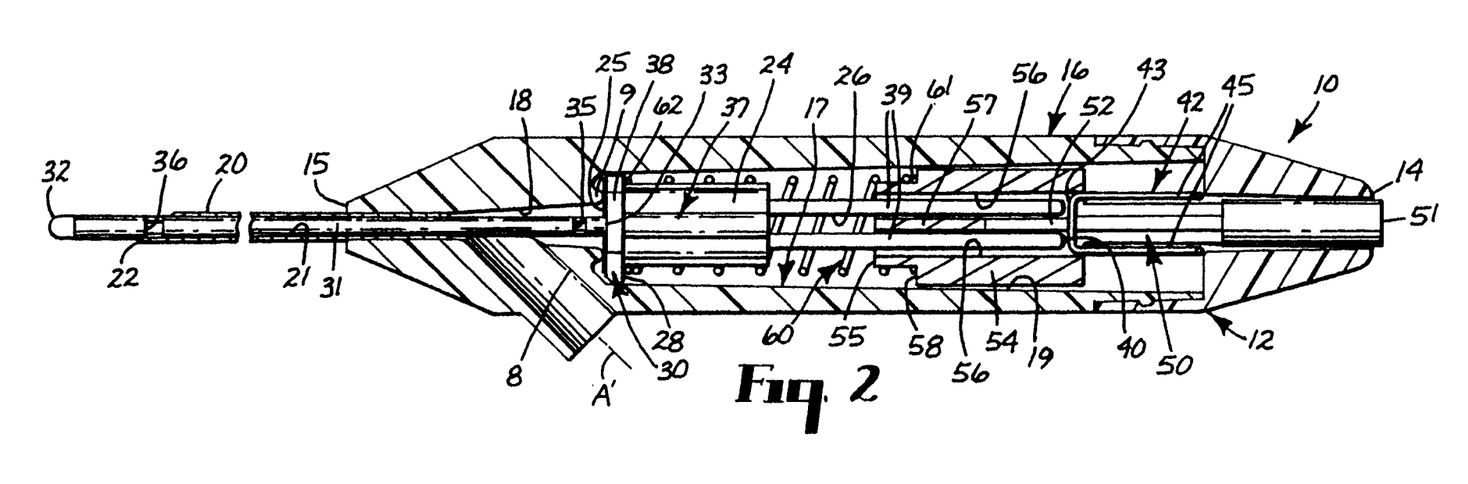
FIG. 2 is a top side view of the pneumoneedle of FIG. 1 with portions broken away to illustrate a fluid conduit for affording passage of fluid such as insufflating gas.

Also preferably, the latching members 39 comprise a pair of spaced guide members defining a groove therebetween (FIGS. 1 and 2). The reset button 50 comprises a body portion 54 having an inner end 55 opposite the exposed end 51, a pair of slots 56 for receiving the guide members e.g. (39), and a reinforcing rib 57 adapted to be received in the groove 26 between the guide members. As best seen in FIG. 1, preferably the sealing flange 38 may include a groove which is adapted to abut a rib (not shown) in the housing 12 for ease of assembly of the product. Also, the sealing flange 38 includes flat surfaces which abut flat surfaces on the housing 12 to restrict rotation of the housing protector 31 relative to the housing 12.

The body portion 54 of the reset button 50 has a notch surface 58 generally adjacent the inner end 55 and an opposite shoulder surface 59 axially spaced from the notch surface 58 and disposed closer to the inner end 55 than the lock release shoulder surface 53. The coil spring 60 is situated about the housing axis A and has first 61 and second 62 ends with the first end 61 fixed to the notch surface 58 of the reset button 50 and with the second end 62 fixed to the surface 28 of the sealing flange 38 of the carrier 37 opposite its sealing flange surface.

OPERATION

The operation of the pneumoneedle 10 will now be described with reference to FIGS. 3 through 6 which sequentially illustrate its operation. When the reset button 50 is in the latched position and the protector assembly 30 is in the protecting position (e.g. the position shown in FIG. 6), manual movement of the reset button 50 toward the reset position will cause the lock release camming surface 52 of the reset button 50 to move the locking pawl spring 42 from the locking position toward the release position and will then allow the locking pawl spring 42 to engage the lock release shoulder surface 53 (e.g. the position shown in FIG. 3).

In the position shown in FIG. 3, the reset button member 50 is in the reset or armed position. In this position, the protector 31 is now free to move relative to the cannula 20 to afford piercing of tissue 2 by the cannula 20. When the reset button member 50, the pawl spring 42, and the protector assembly are in the positions shown in FIG. 3, the pneumoneedle is ready to be pressed against the tissue 2 of a patient.

FIG. 4 illustrates the pneumoneedle 10 just after it is initially pressed against tissue 2. When the protector 31 is pressed against the tissue 2, the resistance of the tissue 2 will cause the protector assembly 30 to move axially toward the retracted position (e.g. deflect toward front end 14 of housing 12). Such movement of the assembly 30 causes the camming surfaces 41 on the carrier 37 to move the locking pawl spring 42 away from engagement with the lock release shoulder surface 53.

After the camming surfaces 41 of the carrier 37 move the locking pawl spring 42 from the locking position toward the release position, but before the end 43 of the locking pawl spring 42 engages the end surface 40, the distal end 43 of the locking pawl spring 42 engages the opposite shoulder surface 59 of the reset button 50. In this position, the reset button member 50 is in a "triggered" position which is between the latched and armed positions. Compare the position of exposed end 51 in FIG. 3 (generally the reset or armed position), FIGS. 4 and 5 (generally the triggered position), and FIG. 6 (generally the latched position).

As the cannula 20 moves through the tissue 2 (e.g. the abdominal wall and peritoneum), the resistance from the tissue 2 will cause the protector assembly 30 to deflect and assume generally the position shown in FIG. 5.

Once the resistance of the tissue 2 ends (such as when the protector 31 enters the abdominal cavity), the protector assembly 30 will be moved by the spring 60 from the position shown in FIG. 5 to the position shown in FIG. 6. The spring 60 also moves the reset button member 50 to the position shown in FIG. 6. Thus, between the positions shown in FIGS. 5 and 6, the protector assembly 30 moves to the protecting position and the pawl spring 42 moves to the locking position.

It should be noted that, in order to get from the configuration of elements in FIG. 6 to the configuration of elements of FIG. 3, a user simply manually presses the reset button member 50 toward the housing 12. Additionally, movement of the reset button member 50 from the triggered position to the latched position causes a collision between a portion of the body portion 54 and a portion of the inner surface 17 of the housing 12 thereby creating an audible sound or a tactile feel to a user which assists in indicating whether the protector assembly 30 is in the protecting position.

The present invention has now been described with reference to several embodiments thereof. It will be apparent to those skilled in the art that many changes or additions can be made in the embodiments described without departing from the scope of the present invention. For example, the coil spring 60 may be replaced by a suitable biasing means such as a pair of coil springs. Thus, the scope of the present invention should not be limited to the structures described in this application, but only by structures described by the language of the claims and the equivalents of those structures.

What is claimed is:

1. A safety pneumoneedle through which the abdomen can be inflated with fluid such as insufflating gas, said pneumoneedle comprising:

an elongate housing having a longitudinal axis, front and rear ends, exterior surfaces generally cylindrical about said axis and adapted to be manually grasped in a dart-like fashion, inner surfaces defining an elongate cavity extending axially between said front and rear ends of said housing, said cavity including a fluid passageway portion adjacent said rear end, and an actuator portion adjacent said front end, said actuator portion having a larger diameter than said fluid passageway portion at a juncture of said fluid passageway and actuator portions and said inner surface defining a sealing surface around the fluid passageway portion at the juncture between said portions, said cavity opening through the exterior surfaces of said housing generally adjacent the front and rear ends of the housing, said housing having a fluid conduit communicating with said fluid passageway portion of said elongate cavity, and having an axis disposed generally at an angle relative to the longitudinal axis of said housing, said fluid conduit opening through the exterior surface of said housing between the front and rear ends of said housing generally near the fluid passageway portion, a tubular elongate cannula having an inner surface defining a through passageway, a proximal end sealingly and fixedly attached to the rear end of said housing with said through passageway communicating with said fluid passageway portion, a sharpened distal end adapted to pierce tissue, and a predetermined length between said proximal and distal ends;

a protector assembly comprising:

a tubular elongate protector having inner surfaces defining a passageway, an outer surface, a closed blunt distal end, and an opposite proximal end, said protector having a length exceeding the predetermined length of said cannula between said proximal and distal ends, said protector being mounted for longitudinal sliding movement within the passageway of said cannula and having axially spaced proximal and distal fluid apertures extending between said protector's inner and outer surfaces and opening into said passageway adjacent said blunt distal and opposite proximal ends respectively, a carrier fixedly attached to said proximal end of said protector and disposed within said actuator portion of said housing cavity, said carrier having a sealing flange with a sealing flange surface at the juncture between said protector and said carrier adapted for abutting said sealing surface of said housing and having latching members extending axially of said housing cavity toward said front end, said latching members having a first abutment end surface disposed generally at a right angle with respect to said axis, and including a camming surface disposed at an acute angle with respect to said axis adjacent and intersecting said first abutment end surface;

said protector assembly being axially slidable within said housing cavity relative to said cannula between a protecting position with the blunt distal end of the protector extending beyond the sharp distal end of the cannula to restrict engagement between tissue and said sharp distal end of the cannula, with said sealing flange in sealing engagement with said sealing surface of said housing, and with said distal fluid aperture of said protector disposed beyond and spaced from said distal end of said cannula and with said proximal fluid aperture of said protector disposed within said fluid passageway portion of said housing cavity, and a retracted position with portions of said sharp distal end of said cannula extending beyond said blunt distal end of said protector to afford puncture of tissue;

latching and release means for positively locking said protector in said protecting position after said cannula has pierced tissue and for releasing the protector after it has been locked in the protecting position, said latching and release means comprising:

a locking pawl spring having proximal and distal ends, said locking pawl spring being disposed within said actuator portion of said housing, and said locking pawl spring being fixedly attached at its proximal end to said housing, said locking pawl spring being mounted for movement between a locking position with the distal end of the pawl spring engaged with the first abutment end surface of the latching members to prevent axial movement of the protector relative to said cannula and to lock the protector in the protecting position, and a release position with the distal end of the locking pawl spring spaced from the first abutment end of the latching members to afford relative axial-movement between the protector and the cannula to afford piercing of tissue by the sharp end of the cannula, said locking pawl spring being biased toward said locking position;

a reset button member having an exposed end adapted to be manually pressed, a lock release camming surface disposed at an acute angle with respect to said housing axis, and a lock release shoulder surface disposed generally at a right angle with respect to said housing axis and intersecting said lock release camming surface, said lock release shoulder surface being adapted to retain said locking pawl spring in the release position until said cannula pierces tissue, portions of said reset button being axially slidable within said actuator portion of said cavity for movement between a latched position with the exposed end of the reset button spaced from the front end of the housing and a reset position with the exposed end of the reset button closer to the front end of the housing than in the latched position;

biasing means for biasing said protector toward said protecting position and for biasing said reset button toward said latched position;

wherein when said reset button is in said latched position and said protector assembly is in said protecting position, manual movement of said reset button toward said reset position will cause said lock release camming surface of said reset button to move said locking pawl spring from said locking position toward said release position and will then allow said locking pawl spring to engage said lock release shoulder surface to afford movement of the protector relative to the cannula, and then when said protector is pressed against tissue, the resistance of the tissue will cause said protector assembly to move axially toward said retracted position to afford piercing tissue, and will cause said camming surfaces on said latching members to move said locking pawl spring away from engagement with said lock release shoulder surface to thereby afford movement of said locking pawl spring from said release position toward said locking position when said biasing means causes said protector assembly to move to said protecting position after resistance from the tissue is released upon movement of the cannula into the abdominal cavity.

2. A safety pneumoneedle according to claim 1 wherein said locking pawl spring comprises a monolithic wire member having a pair of base portions extending generally at an angle relative to the longitudinal axis of said housing cavity, a pair of neck portions extending at an angle relative to said base portions and an end portion extending between said neck portions.

3. A safety pneumoneedle according to claim 1 wherein said carrier comprises a carriage portion;

said sealing flange has a surface opposite said sealing surface, said latching members comprise a pair of spaced guide members defining a groove therebetween; and said reset button comprises a body portion having an inner end opposite said exposed end, a pair of slots for receiving said guide members, and a reinforcing rib adapted to be received in the groove between said guide members.

4. A safety pneumoneedle according to claim 3 wherein said body portion of said reset button has a notch surface generally adjacent said inner end and an opposite shoulder surface axially spaced from said notch surface and disposed closer to said inner end than said lock release shoulder surface;

said biasing means comprises a coil spring situated about said housing axis and having first and second ends with the first end fixed to said notch surface of said reset button and with said second end fixed to said surface of said sealing flange of said carrier opposite its sealing flange surface, and wherein after said camming surface of said protector assembly moves said locking pawl spring from engagement with lock release shoulder surface, but before said locking pawl spring engages said first abutment end surface of said protector assembly, said distal end of said locking pawl spring engages said opposite shoulder surface of said reset button until said protector assembly moves to said protecting position.

5. A safety pneumoneedle according to claim 1 wherein movement of the reset button member to the latched position causes a collision between a portion said protector assembly and a portion of said inner surface of the housing thereby creating an audible sound for a user.

6. A safety pneumoneedle according to claim 1 wherein movement of the reset button member to the latched position causes a collision between a portion said protector assembly and a portion of said inner surface of the housing thereby creating a tactile feel for a user.

7. A safety pneumoneedle according to claim 1 wherein said sealing flange of said carrier includes an elastomeric sealing member.

8. A safety pneumoneedle according to claim 7 wherein said elastomeric material is a silicone.

9. A safety pneumoneedle according to claim 1 further including a stopcock valve in fluid communication with said fluid conduit.

10. A safety pneumoneedle according to claim 1 wherein said exterior surfaces of said housing include a structured surface for enhancing manual grasping of said housing.

11. A safety pneumoneedle according to claim 1 wherein the locking pawl spring and at least portions of the housing are a unitary, monolithic structure constructed from an injection molded polymer material.

12. A safety pneumoneedle through which the abdomen can be inflated with fluid such as insufflating gas, said pneumoneedle comprising:

an elongate housing having a longitudinal axis, front and rear ends, exterior surfaces adapted to be manually grasped in a dart-like fashion, inner surfaces defining an elongate cavity extending axially between said front and rear ends of said housing, said cavity including a fluid passageway portion adjacent said rear end, and an actuator portion adjacent said front end, said inner surfaces defining a sealing surface around a fluid passageway portion at the juncture between said fluid passageway and actuator portions, said housing having a fluid conduit communicating with said fluid passageway portion of said elongate cavity, and having an axis disposed generally at an angle relative to the longitudinal axis of said housing, said fluid conduit opening through the exterior surface of said housing between the front and rear ends of said housing generally near the fluid passageway portion, an elongate cannula having an inner surface defining a through passageway, a proximal end sealingly and fixedly attached to the rear end of said housing with said through passageway communicating with said fluid passageway portion, a sharpened distal end adapted to pierce tissue;

a protector assembly comprising:
an elongate protector having inner surfaces defining a passageway, a closed blunt distal end, and an opposite proximal end, said protector being mounted for longitudinal sliding movement within the passageway of said cannula and having axially spaced proximal and distal fluid apertures, a carrier fixedly attached to said proximal end of said protector and disposed within said actuator portion of said housing cavity, said carrier having a sealing flange with a sealing flange surface at the juncture between said protector and said carrier adapted for abutting said sealing surface of said housing and having latching members extending axially toward said front end, said latching members having a first abutment end surface disposed generally at a right angle with respect to said axis;

said protector assembly being axially slidable within said housing cavity relative to said cannula between a protecting position with the blunt distal end of the protector extending beyond the sharp distal end of the cannula to restrict engagement between tissue and said sharp distal end of the cannula, with said sealing flange in sealing engagement with said sealing surface of said housing, and with said distal fluid aperture of said protector disposed beyond and spaced from said distal end of said cannula and with said proximal fluid aperture of said protector disposed within said fluid passageway portion of said housing cavity, and a retracted position with portions of said sharp distal end of said cannula extending beyond said blunt distal end of said protector to afford puncture of tissue; and latching and release means for positively locking said protector in said protecting position and for releasing the protector after it has been locked in the protecting position.

13. A pneumoneedle according to claim 12 wherein said latching members each include a camming surface disposed at an acute angle with respect to said axis adjacent and intersecting the first abutment end surface of the respective latching member, said latching and release means comprise a locking pawl spring having proximal and distal ends, said locking pawl spring being disposed within said actuator portion of said housing and said locking pawl spring being fixedly attached at its proximal end to said housing;

said locking pawl spring being mounted for movement between a locking position with the distal end of the pawl spring engaged with the first abutment end surface of said latching members to prevent axial movement of the protector relative to said cannula and to lock the protector in the protecting position, and a release position with the distal end of the locking pawl spring spaced from the first abutment end surface of the latching members to afford relative axial movement between the protector and the cannula to afford piercing of tissue by the sharp end of the cannula, said locking pawl spring being biased toward said locking position;

a reset button member having an exposed end adapted to be manually pressed, a lock release camming surface disposed at an acute angle with respect to said housing axis, and a lock release shoulder surface disposed generally at a right angle with respect to said housing axis and intersecting said lock release camming surface, said lock release shoulder surface being adapted to retain said locking pawl spring in the release position until said cannula pierces tissue, portions of said reset button being axially slidable within said actuator portion of said cavity for movement between a latched position with the exposed end of the reset button spaced from the front end of the housing and a reset position with the exposed end of the reset button closer to the front end of the housing than in the latched position;

biasing means for biasing said protector toward said protecting position and for biasing said reset button toward said latched position; and wherein when said reset button is in said latched position and said protector assembly is in said protecting position, manual movement of said reset button toward said reset position will cause said lock release camming surface of said reset button to move said locking pawl spring from said locking position toward said release position and will then allow said locking pawl spring to engage said lock release shoulder surface to afford movement of the protector relative to the cannula, and then when said protector is pressed against tissue, the resistance of the tissue will cause said protector assembly to move axially toward said retracted position to afford the piercing of tissue by said sharpened end of said cannula, and will cause said camming surfaces on said latching members to move said locking pawl spring away from engagement with said lock release shoulder surface to thereby afford movement of said locking pawl spring from said release position toward said locking position when said biasing means causes said protector assembly to move to said protecting position after resistance from the tissue is released.

14. A pneumoneedle according to claim 13 wherein said carrier comprises a carriage portion;

said sealing flange has a surface opposite said sealing surface;

said latching members comprise a pair of spaced guide members defining a groove therebetween; and said reset button comprises a body portion having an inner end opposite said exposed end, a pair of slots for receiving said guide members, and a reinforcing rib adapted to be received in the groove between said guide members.

15. A safety pneumoneedle according to claim 14 wherein said body portion of said reset button has a notch surface generally adjacent said inner end and an opposite shoulder surface axially spaced from said notch surface and disposed closer to said inner end than said lock release shoulder surface, said biasing means comprises a coil spring situated about said housing axis and having first and second ends with the first end fixed to said notch surface of said reset button and with said second end fixed to said surface of said sealing flange of said carrier opposite its sealing flange surface, and wherein after said camming surface of said protector assembly moves said locking pawl spring from engagement with said lock release shoulder surface, but before said locking pawl spring engages said first abutment end surface of said protector assembly, said distal end of said locking pawl spring engages said opposite shoulder surface of said reset button until said protector assembly moves to said protecting position.

16. A safety pneumoneedle according to claim 13 wherein the locking pawl spring and at least portions of the housing are a unitary, monolithic structure constructed from an injection molded polymer material.

17. A safety pneumoneedle through which the abdomen can be inflated with fluid such as insufflating gas, said pneumoneedle comprising:

a housing having a longitudinal axis, front and rear ends, exterior surfaces adapted to be manually grasped, inner surfaces defining an elongate cavity extending axially between said front and rear ends of said housing, said cavity including a fluid passageway portion adjacent said rear end, and an actuator portion adjacent said front end, said inner surfaces defining a sealing surface around the fluid passageway portion at a juncture of said fluid passageway and actuator portions, said housing having a fluid conduit communicating with said fluid passageway portion of said elongate cavity and having an axis disposed generally at an angle relative to the longitudinal axis of said housing;

a non-removable cannula having a proximal end sealingly and fixedly attached to said housing, inner surfaces defining a passageway, a sharpened distal end adapted to pierce tissue;

a protector assembly comprising:

an elongate protector having a closed blunt distal end, and an opposite proximal end, said protector being mounted for longitudinal sliding movement within the passageway of said cannula, and means for passage of fluid, a carrier fixedly attached to said proximal end of said protector and disposed within said actuator portion of said housing cavity, said carrier having a sealing flange with a sealing flange surface at the juncture between said protector and said carrier adapted for abutting said sealing surface of said housing and having latching members extending axially toward said front end, said latching members having a first abutment end surface;

said protector assembly being axially slidable within said housing cavity relative to said cannula between a protecting position with the blunt distal end of the protector extending beyond the sharp distal end of the cannula to restrict engagement between tissue and said sharp distal end of the cannula, and with said sealing flange in sealing engagement with said sealing surface of said housing, and a retracted position with portions of said sharp distal end of said cannula extending beyond said blunt distal end of said protector to afford puncture of tissue;

a locking pawl spring disposed within the actuator portion of said housing and fixedly attached at a proximal end to said housing and having a distal end, said locking pawl spring being mounted for movement between a locking position with the distal end of the pawl spring engaged with the first abutment end surface of the latching members to prevent axial movement of the protector relative to said cannula and to lock the protector in the protecting position, and a release position with the distal end of the locking pawl spring spaced from the first abutment end surface of the latching members to afford relative axial movement between the protector and the cannula to afford piercing of tissue by the sharp end of the cannula, said locking pawl spring being biased toward said locking position;

a reset button member having an exposed end adapted to be manually pressed, a lock release camming surface disposed at an acute angle with respect to said housing axis, and a lock release shoulder surface disposed generally at a right angle with respect to said housing axis and intersecting said lock release camming surface, portions of said reset button being axially slidable within said actuator portion of said cavity for movement between a latched position with the exposed end of the reset button spaced from the front end of the housing and a reset position with the exposed end of the reset button closer to the front end of the housing than in the latched position; and biasing means for biasing said protector toward said protecting position and for biasing said reset button toward said latched position.

18. A safety pneumoneedle through which the abdominal cavity can be inflated with fluid such as insufflating gas, said pneumoneedle comprising:
a housing having front and rear ends, exterior surfaces adapted to be manually grasped, inner surfaces defining an elongate cavity having a fluid passageway portion;
a non-removable cannula having a proximal end sealingly and fixedly attached to said housing, and a sharpened distal end adapted to pierce tissue;
a protector assembly having a closed blunt distal end, a first abutment end surface;
said protector assembly being movable relative to said cannula between a protecting position with the blunt distal end of the protector assembly extending beyond the sharp distal end of the cannula to restrict engagement between tissue and said sharp distal end of the cannula, and a retracted position with portions of said sharp distal end of said cannula extending beyond said blunt distal end of said protector assembly to afford puncture of tissue; and
latching and release means for positively locking said protector assembly in said protecting position and for releasing the protector assembly after it has been locked in the protecting position, said latching and release means comprising a locking pawl spring adapted to abut the first abutment end surface of the protector assembly.

19. A pneumoneedle according to claim 18 wherein said protector assembly includes a camming surface said latching and release means comprise the locking pawl spring fixedly attached at a proximal end to said housing and having a distal end, said locking pawl spring being mounted for movement between a locking position with the distal end of the pawl spring engaged with the first abutment end surface of the protector assembly to prevent movement of the protector assembly relative to said cannula and to lock the protector assembly in the protecting position, and a release position with the distal end of the locking pawl spring spaced from the first abutment end surface of the protector assembly to afford relative movement between the protector assembly and the cannula to afford piercing of tissue by the sharp end of the cannula, said locking pawl spring being biased toward said locking position;

a reset button member having an exposed end adapted to be manually pressed, a lock release camming surface, and a lock release shoulder surface, portions of said reset button being slidable within said cavity for movement between a latched position with the exposed end of the reset button spaced from the front end of the housing and a reset position with the exposed end of the reset button closer to the front end of the housing than in the latched position;

biasing means for biasing said protector assembly toward said protecting position and for biasing said reset button toward said latched position; and wherein when said reset button is in said latched position and said protector assembly is in said protecting position, manual movement of said reset button toward said reset position will cause said lock release camming surface of said reset button to move said locking pawl spring from said locking position toward said release position and will then allow said locking pawl spring to engage said lock release shoulder surface to afford movement of the protector assembly relative to the cannula, and then when said blunt end of said protector assembly is pressed against tissue, the resistance of the tissue will cause said protector assembly to move toward said retracted position to afford the piercing of tissue by said sharpened end of said cannula, and will cause said camming surface on said protector assembly to move said locking pawl spring away from engagement with said lock release shoulder surface to thereby afford movement of said locking pawl spring from said release position toward said locking position when said biasing means causes said protector assembly to move to said protecting position after resistance from the tissue is released upon movement of the cannula into the abdominal cavity.

20. A pneumoneedle according to claim 18 wherein said cavity of said housing includes a fluid conduit disposed at an angle relative to a longitudinal axis of said housing.

21. A pneumoneedle according to claim 19 wherein said protector assembly comprises a carrier including a carriage portion, a sealing flange and a pair of latching members;
said sealing flange has a sealing surface;
said latching members comprise a pair of spaced guide members defining a groove therebetween; and
said reset button comprises a body portion having an inner end opposite said exposed end, a pair of slots for receiving said guide members, and a reinforcing rib adapted to be received in the groove between said guide members.

22. A safety pneumoneedle according to claim wherein said body portion of said reset button has a notch surface generally adjacent said inner end and an opposite shoulder surface spaced from said notch surface and disposed closer to said inner end than said lock release shoulder surface,
said biasing means comprises a coil spring having first and second ends with the first end fixed to said notch surface of said reset button and with said second end fixed to said sealing flange,
wherein after said camming surface of said protector assembly moves said locking pawl spring from engagement with said lock release shoulder surface, but before said locking pawl spring engages said first abutment end surface of said protector assembly, said distal end of said locking pawl spring engages said opposite shoulder surface of said reset button until said protector assembly moves to said protecting position.

23. A safety pneumoneedle according to claim 19 wherein the locking pawl spring and at least portions of the housing are a unitary, monolithic structure constructed from an injection molded polymer material.

24. A safety pneumoneedle through which the abdomen can be inflated with fluid such as insufflating gas, said pneumoneedle comprising:
- a housing having front and rear ends, exterior surfaces adapted to be manually grasped, inner surfaces defining an elongate cavity having a fluid passageway portion,
- a non-removable cannula having a proximal end sealingly and fixedly attached to said housing, and a sharpened distal end adapted to pierce tissue;
- a protector assembly having a closed blunt distal end, a first abutment end surface;
  - said protector assembly being movable relative to said cannula between a protecting position with the blunt distal end of the protector assembly extending beyond the sharp distal end of the cannula to restrict engagement between tissue and said sharp distal end of the cannula, and a retracted position with portions of said sharp distal end of said cannula extending beyond said blunt distal end of said protector assembly to afford puncture of tissue;
- a pawl spring for engaging said first abutment end surface to positively lock said protector assembly in said protecting position; and
- a reset button member for releasing the protector assembly after it has been locked in the protecting position.

25. A safety pneumoneedle through which the abdomen can be inflated with fluid such as insufflating gas, said pneumoneedle comprising:
- a housing having front and rear ends, exterior surfaces adapted to be manually grasped,
- a non-removable cannula having a proximal end sealingly and fixedly attached to said housing, and a sharpened distal end adapted to pierce tissue;
- a protector assembly having a closed blunt distal end, said protector assembly being movable relative to said cannula between a protecting position with the blunt distal end of the protector assembly extending beyond the sharp distal end of the cannula to restrict engagement between tissue and said sharp distal end of the cannula, and a retracted position with portions of said sharp distal end of said cannula extending beyond said blunt distal end of said protector assembly to afford puncture of tissue; and
- latching means including a locking pawl spring for positively locking said protector assembly in said protecting position.

26. A pneumoneedle according to claim 25 wherein said pneumoneedle includes release means for releasing the protector assembly after it has been locked in the protecting position.

27. A pneumoneedle through which the abdomen can be inflated with fluid such as insufflating gas, said pneumoneedle comprising:
- a housing having exterior surfaces adapted to be manually grasped, and inner surfaces defining an elongate cavity having a fluid passageway portion,
- a cannula having a sharpened distal end for piercing tissue;
- a protector having a blunt distal end,
- a passage in fluid communication with said fluid passageway portion for affording passage of insufflating gas through the pneumoneedle,
- the cannula and protector being mounted for relative movement between a protecting position with the blunt distal end of the protector extending beyond the sharp distal end of the cannula to restrict engagement between tissue and the sharp distal end of the cannula, and a retracted position with portions of the sharp distal end of the cannula extending beyond the blunt distal end of the protector to afford puncture of tissue; and
- a positive locking latch having a locking pawl spring for locking the cannula and protector in the protecting position.

28. A pneumoneedle according to claim 27 further including a release for releasing the latch when the cannula and protector are locked in the protecting position to afford relative movement between the cannula and the protector.

29. A pneumoneedle according to claim 27 wherein the locking pawl spring that locks the cannula and protector in the protecting position after the cannula has pierced tissue.

30. A pneumoneedle according to claim 28 wherein the release comprises a button member that is movable relative to the housing.

* * * * *

UNITED STATES PATENT AND TRADEMARK OFFICE
CERTIFICATE OF CORRECTION

PATENT NO.: 5,374,252

DATED: December 20, 1994

INVENTOR(S): Thomas F. Banks and William A. Mittelstadt

It is certified that error appears in the above-identified patent and that said Letters Patent is hereby corrected as shown below:

Col. 18, line 57, after "claim" insert --21--.

Signed and Sealed this

Twenty-ninth Day of August, 1995

Attest:

BRUCE LEHMAN

Attesting Officer        Commissioner of Patents and Trademarks